United States Patent
Yekta et al.

(10) Patent No.: US 8,063,386 B2
(45) Date of Patent: Nov. 22, 2011

(54) TIME RESOLVED FLUORESCENT IMAGING SYSTEM

(75) Inventors: Ahmad Yekta, Somerset, NJ (US); Pavel A. Fomitchov, New York, NY (US); Joseph Masino, Howell, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 96 days.

(21) Appl. No.: 12/517,653

(22) PCT Filed: Jan. 23, 2008

(86) PCT No.: PCT/US2008/051752
§ 371 (c)(1),
(2), (4) Date: Jun. 4, 2009

(87) PCT Pub. No.: WO2008/094794
PCT Pub. Date: Aug. 7, 2008

(65) Prior Publication Data
US 2010/0090127 A1    Apr. 15, 2010

Related U.S. Application Data

(60) Provisional application No. 60/887,230, filed on Jan. 30, 2007.

(51) Int. Cl.
*G01N 21/64* (2006.01)
(52) U.S. Cl. ................................. 250/459.1
(58) Field of Classification Search ............ 250/584, 250/585, 586, 459.1
See application file for complete search history.

(56) References Cited

U.S. PATENT DOCUMENTS

| | | | |
|---|---|---|---|
| 5,523,573 A | 6/1996 | Hanninen et al. | |
| 6,504,167 B2 * | 1/2003 | Ikami | 250/584 |
| 7,794,661 B2 * | 9/2010 | Ikami | 422/82.08 |
| 2002/0001075 A1 | 1/2002 | Tsien et al. | |
| 2003/0160151 A1 | 8/2003 | Zarate et al. | |
| 2006/0017001 A1 | 1/2006 | Donders et al. | |

FOREIGN PATENT DOCUMENTS
WO    WO 00/08443    2/2000

OTHER PUBLICATIONS

Austin, R. H., et al., "Rotational diffusion of cell surface components by time-resolved phosphorescence anisotropy," Proc Natl Acad Sci. 76, 5650-5654 (1979).
Bigas, M., et al., "Review of CMOS image sensors," Microelectronics J 37, 433-451 (2006).
Clegg, R. M., "Fluorescence lifetime-resolved imaging: Measuring lifetimes in an image," Methods in Enzymology, 360, 509-542 (2003).
El Gama, A., et al., "CMOS image sensors," IEEE Circuits & Devices 21, 6-20 (2005).
Elson, D., et al., "Time-domain fluorescence lifetime imaging applied to biological tissue," Photochem & Photobio Sci, 3 (8) 795-801 (2004).

(Continued)

*Primary Examiner* — Constantine Hannaher

(57) ABSTRACT

A system and method that allows for time-resolved fluorescent imaging of fluorescent samples. The user is able to receive temporally filtered pictures of the sample with a reduced amount of the scattered excitation light and the short lived background fluorescence. The system allows for adjustment of fluorescent gating time and delay time.

23 Claims, 12 Drawing Sheets

OTHER PUBLICATIONS

Hemmila, I., et al., "Time-resolution in fluorometry technologies, labels and applications in bioanalytical assays," Crit Rev Clin Lab Sci 38, 441-519 (2001).

Hemmila, I., et al., "Progress in lanthanides as luminescent probes," J Fluores 15, 529-542 (2005).

Krishnan, R. V., et al., "Development of multiphoton fluorescence lifetime imaging microscopy (FLIM) system using a streak camera," Rev. Sci. Instrum., 74, 2714-2721 (2003).

Lakowicz, J. R., et al., "Microsecond dynamics of biological macromolecules," Methods Enzym. 323, 473-509 (2000).

Owicki, J. C., "Fluorescence polarization and anisotropy in high throughput screening: perspective and primer," J Biomol Scr 5, 297-306 (2000).

Ramm, P., "Image-based screening: a technology in transition," Curr. Opin. Biotech. 16, 41-48 (2005).

Schauerte, J. A., et al., "Time-resolved room temperature tryptophan phosphorescence in proteins," Methods Enzym., 278, 49-71 (1997).

Seveus, L., et al., "Time-resolved fluorescence imaging of europium chelate label in immunohistochemistry and in situ hybridization," Cytometry, 13, 329-338 (1992).

Soini, A. E., et al., "A new technique for multiparametric imaging microscopy: Use of long decay time photoluminescent labels enables multiple color immunocytochemistry with low channel to-channel crosstalk," Microsc Res Technol, 62, 396-407 (2003).

Subramaniam, V., et al., "Time-resolved tryptophan phosphorescence spectroscopy: A sensitive probe of protein folding and structure," IEEE J of Selected Topics in Quantum Electronics 2, 1107-1114 (1996).

Suhling, K., et al., "Time-resolved fluorescence microscopy," Photochem & Photobio Sci, 4 (1) 13-22 (2005).

Vanderkooi, J. M., et al., "On the prevalence of room temperature protein phosphorescence," Science 236, 568-569 (1987).

Vanderkooi, J. M., Tryptophan phosphorescence from proteins at room temperature, In "Topics in Fluorescence Spectroscopy," vol. 3 Biochemical Applications, Lakowicz JR Edited, Plenum Press, NY, 1992, pp. 113-136.

Van Munster, E. B., et al., "Fluorescence lifetime imaging microscopy (FLIM)," Adv in Biochem Eng / Biotech, 95, 143-175 (2005).

Zhou, X., et al., "High content cellular imaging for drug development," IEEE Sig. Proc. Mag. 23, 170-174 (2006).

\* cited by examiner

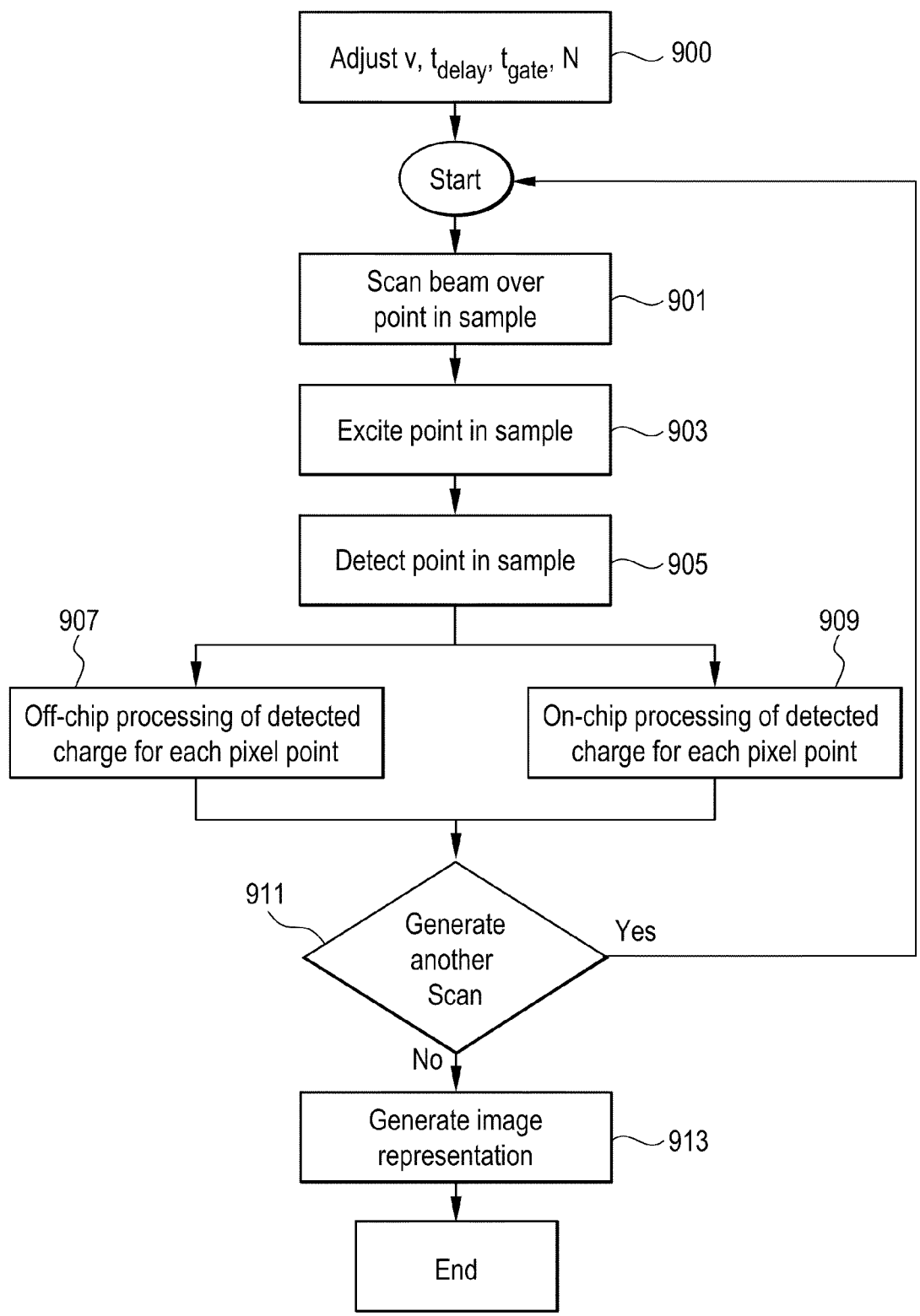

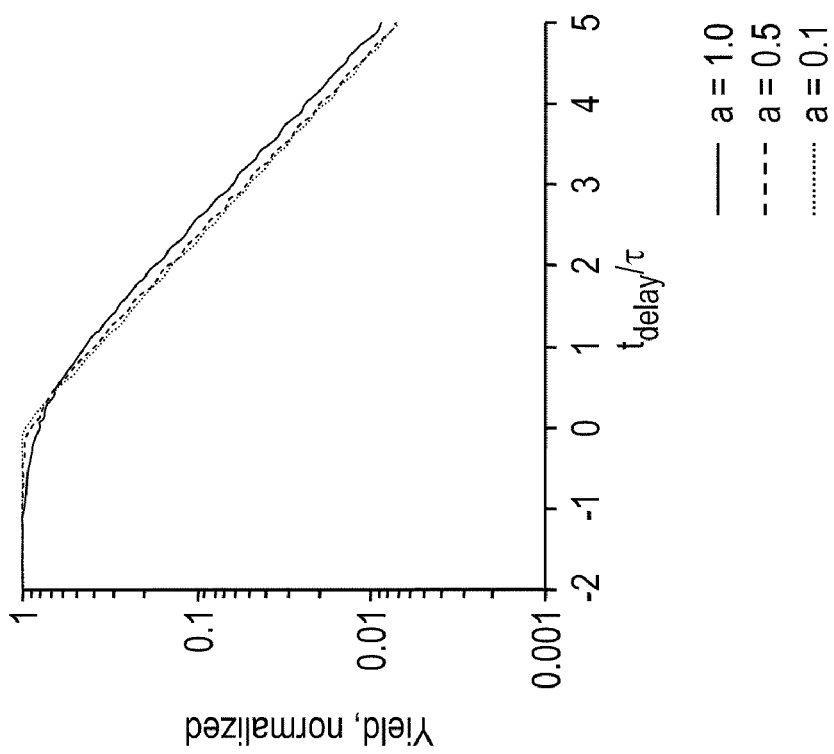
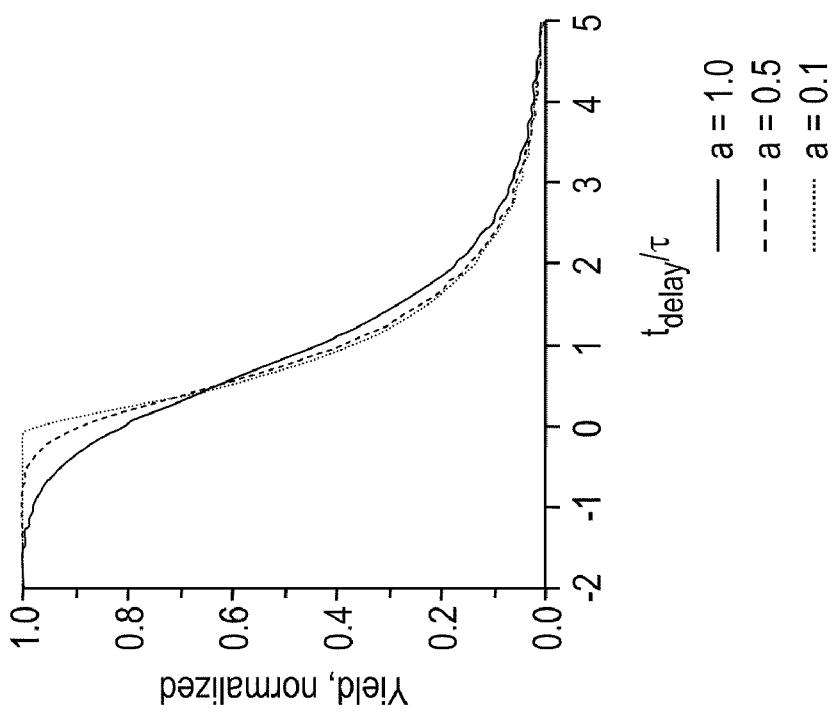
FIG. 10C
FIG. 10D

TIME RESOLVED FLUORESCENT IMAGING SYSTEM

CROSS-REFERENCE TO RELATED APPLICATIONS

This application is a filing under 35 U.S.C. §371 and claims priority to international patent application number PCT/US2008/051752 filed Jan. 23, 2008, published on Aug. 7, 2008, as WO 2008/094794, which claims priority to United States provisional patent application number 60/887,230 filed on Jan. 30, 2007; the entire disclosure of which is incorporated herein by reference in its entirety.

FIELD OF THE INVENTION

This invention relates to time resolved fluorescent imaging systems.

BACKGROUND OF THE INVENTION

Fluorescence detection offers one of the most sensitive methods for quantification of probe molecules in biological and material systems because it can attain near single-molecule sensitivity levels. Consequently the technique is widely used in the assaying of biochemical and cellular systems, and in particular the microscopic imaging of cell-based assay, where rich biological information is provided from multiplexed high-content data (Ramm P, "Image-based screening: a technology in transition," *Curr. Opin. Biotech.* 16, 41-48 (2005); Zhou X and Wong STC, "High content cellular imaging for drug development," *IEEE Sig. Proc. Mag.* 23, 170-174 (2006)).

Attainment of high sensitivity levels requires rejection of background light. In part, background arises from the scatter of the excitation light. Better filtering and separation of excitation and emission lights reduces background, but a small amount can still leak through to the detector. Background also arises from spurious fluorescence, from components of the sample other than the probe of interest, from the sample holder, and from the measuring instrument's optical components. Because of its composite nature, spurious fluorescence generally occurs over a broad range of wavelengths and its removal by spectral filtering is not very effective.

One way of reducing background is by time resolution of the signal, which amounts to temporal filtering of the signal. When the fluorescent probe is appropriately long-lived and the excitation light is pulsed (or modulated with high frequency), test sample fluorescence will last longer than the scattered excitation, or spurious fluorescence. The effect is particularly pronounced with time-resolved fluorescence (TRF) reagents, where by design of chemistry, sample probes have fluorescence lifetimes in the ms ($10^{-3}$ s) to µs ($10^{-6}$ s) time domain (Hemmila I, Laitala V, "Progress in lanthanides as luminescent probes," *J Fluores* 15, 529-542 (2005); Hemmila I, Mukkala V-M, "Time-resolution in fluorometry technologies, labels and applications in bioanalytical assays," *Crit Rev Clin Lab Sci* 38, 441-519 (2001)). In comparison, background from the scattered excitation pulse and spurious fluorescence lasts for a shorter period of time, approximately for the duration of the excitation pulse itself. A key requirement for time resolution of fluorescence is that the duration of the excitation pulse should be less than that of the test compound. Time resolution leads to very significant improvements in sensitivity. In practice, for example, one finds that TRF imagers such as the LEADSEEKER™ manufactured by GE® Healthcare located in Piscataway, N.J. have detection sensitivities some two orders of magnitude higher than the same system in its steady-state fluorescence detection mode.

Apart from the rejection of background light, there are additional advantages to time resolved measurements. Fluorescence is usually measured (or imaged) as steady-state fluorescence (SSF). That is, a steady source of excitation light is used to generate a constant flux of sample fluorescence. The SSF method suffers because of two reasons: (a) The signal depends on the intensity of the excitation source, and the design details of the optical measuring instrument. That is, SSF signal values are dependent on the particulars of the measuring system and hence not reproducible across different laboratories. In contrast, time resolved measurements can yield the mean fluorescence lifetime of the probe, a molecular property which has values independent of the measuring system, and hence reproducible across different laboratories.

Moreover, SSF only gives information on the average state of an excited probe over long time periods. Much more information about the dynamics of a probe and its microenvironment may be obtained if its fluorescence is followed by time-resolution. Examples of dynamics include kinetics of molecular rotation, diffusion, reaction, energy transfer, etc. Of special interest is the rotational depolarization behavior of long-lived TRF reagents. This is because in the usual fluorescence polarization (FP) assays one relies on ns lifetime probes. In this time regime one can only interrogate the rotational dynamics of small-molecules. As a result such FP assays can not detect changes to the structure of a large protein, because the rotational time scales would be too long to affect the polarization of fluorescence. Long-lived TRF reagents however have lifetimes about $10^5$ times longer than ns dyes and can widen the applicability of FP assays, particularly within cell-based systems (Owicki J C, "Fluorescence polarization and anisotropy in high throughput screening: perspective and primer," *J Biomol Scr* 5, 297-306 (2000); Austin R H, Chan S S, Jovin T M, "Rotational diffusion of cell surface components by time-resolved phosphorescence anisotropy," *Proc Natl Acad Sci.* 76, 5650-5654 (1979)).

Yet another application of time-resolved detection is for label-free detection of proteins in biochemical and cellular media. Here one relies on the intrinsic long-lived phosphorescence of cellular proteins (ms and longer), particularly from the tryptophan residues (Vanderkooi J M, Tryptophan phosphorescence from proteins at room temperature, In "Topics in Fluorescence Spectroscopy," Volume 3 Biochemical Applications, Lakowicz J R Edited, Plenum Press, NY, 1992, pp. 113-136; Vanderkooi J M et al., "On the prevalence of room temperature protein phosphorescence," *Science* 236, 568-569 (1987)). Lack of sensitive time-resolved imaging systems has hampered the development of novel assays for the study of in-situ protein folding dynamics (Lakowicz J R, Gryczynski I, Piszczek G, et al., "Microsecond dynamics of biological macromolecules," *Methods Enzym.* 323, 473-509 (2000); Schauerte J A, Steel D G, Gafni A, "Time-resolved room temperature tryptophan phosphorescence in proteins," *Methods Enzym.*, 278, 49-71 (1997); Subramaniam V, Gafni A, Steel D G, "Time-resolved tryptophan phosphorescence spectroscopy: A sensitive probe of protein folding and structure," *IEEE J of Selected Topics in Quantum Electronics* 2, 1107-1114 (1996)).

Time resolved measurement has been segmented into two areas, represented by the two modalities of imaging, FLIM and TRF: (a) Systems that measure in the ns to µs time regime. When applied to imaging, these are called fluorescent lifetime imager (FLIM) systems, where in the output image the value of each pixel represents the mean lifetime of the sample emission from that location. That is, images are 'lifetime' images, and are not intensity based; (b) Systems that measure in the μs to ms time regime, usually used in conjunction with bioassay TRF reagents (above refs.). No commercial cell imaging system is known in this area.

The ns time domain instrumentation for time resolved imaging has been developed for use with probes such as FITC, Rhodamine, EGFP. The systems operate by two approaches: fast pulsed laser excitation of the sample followed by fast detection (e.g., camera/image intensifier combinations), or more commonly, fast electronic modulation of a steady excitation source (e.g., laser and or diodes) in conjunction with a fast detector employing phase shift electronics (van Munster E B, Gadella T W J, "Fluorescence lifetime imaging microscopy (FLIM)," *Adv in Biochem Eng/Biotech*, 95, 143-175 (2005); Suhling K, French P M W, Phillips D, "Time-resolved fluorescence microscopy," *Photochem & Photobio Sci*, 4 (1) 13-22 (2005); Elson D et al., "Time-domain fluorescence lifetime imaging applied to biological tissue," *Photochem & Photobio Sci*, 3 (8) 795-801 (2004); Krishnan R V et al., "Development of multiphoton fluorescence lifetime imaging microscopy (FLIM) system using a streak camera," *Rev. Sci. Instrum.*, 74, 2714-2721 (2003); Clegg R M, "Fluorescence lifetime-resolved imaging: Measuring lifetimes in an image," *Methods in Enzymology*, 360, 509-542 (2003)). Examples of prior art disclosures include WO2000008443(A1) by P Bastiaens et al. employing modulated excitation and emission constructs, commercialized through Lambert Instruments, Leutingewolde, the Netherlands (http://www.lambert-instruments.com/), and the Hamamatsu C9136 lifetime imaging microscopy system (http://sales.hamamatsu.com/), employing ps pulsed lasers and fast streak cameras, disclosed in Krishnan R V et al., "Development of multiphoton fluorescence lifetime imaging microscopy (FLIM) system using a streak camera," *Rev. Sci. Instrum.*, 74, 2714-2721 (2003). These systems can create high-content cellular lifetime images but are all expensive, complex, and difficult to operate and maintain.

The μs to ms time domain instrumentation systems for time resolved measurement have been developed for use with the long-lived TRF reagents (above refs.), and are known as TRF readers (or TRF imagers). The readers rely on detection with photomultiplier tubes (PMT). They have slow throughputs because they read microtiter plates, one well at a time. Another class of systems relies on macro-imaging of microtiter plates, as exemplified by the LEADSEEKER™ Multimodality Imaging System (GE® Healthcare Bio-Sciences, Piscataway, N.J., disclosed in US patent publication no. 2003-0160151) and the VIEWLUX™ ultra HTS Microplate Imager (PerkinElmer Life And Analytical Sciences, Inc., Wellesley, Mass.). The macro-imagers use a charge-coupled device (CCD) to capture the images. They have higher throughput than the PMT-based readers because all wells of a microtiter plate are imaged at once. Most TRF readers (or imagers) operate by using a μs flash lamp to excite the sample, along with electronic gating of the detector to read the sample fluorescence after a delay time of few us, for a gate duration of about 1-3 emission lifetime. In some systems the flash lamp is replaced by the mechanical chopping of a steady light source and the emission itself. CCDs are relatively slow-reading devices so that the gating of TRF imagers is accomplished outside the detector, either by an optoelectronic shutter (as in the LEADSEEKER™), or by a mechanical chopper (as in the VIEWLUX™)

The key advantage of TRF imagers is in reduction of the contribution of background light to overall signal intensity. The images created are intensity images and the gated signal is dependent on the instrumental settings. TRF imagers are usually not used as FLIM lifetime measuring systems. However, creation of a lifetime image from TRF imagers is possible in principle. It requires acquisition of multiple images with different gating times (or delay times), and further mathematical processing of the image data for each pixel position to extract a mean lifetime value for that position.

Integration of the TRF technology into microscopy for high content imaging has been disclosed in U.S. Pat. No. 5,523,573, and Seveus L et al., "Time-resolved fluorescence imaging of europium chelate label in immunohistochemistry and in situ hybridization," *Cytometry*, 13, 329-338 (1992); Soini A E et al., "A new technique for multiparametric imaging microscopy: Use of long decay time photoluminescent labels enables multiple color immunocytochemistry with low channel to-channel crosstalk," *Microsc Res Technol*, 62, 396-407 (2003). In this approach, the excitation light is pulsed by use of, either a laser or flash lamp, or a revolving shutter in front of a steady lamp, and detection is gated by use of timing electronics and a mechanical chopper in front of the emission light. These components add cost and complexity to the base microscopic imaging system. Moreover, the uses of a rotating chopper limits the detection system to the ms time domain and longer, while introducing safety concerns and the possibility of image distortion from mechanical vibrations. For these reasons, at present no commercial high-content TRF microscopic imagers are offered on the market.

Therefore, there is a need for a system that overcomes the expense and complexities of FLIM systems and the limitations of TRF imagers by devising a system that adds time resolution capability with little additional cost to the base steady-state fluorescence imaging system.

BRIEF SUMMARY OF THE INVENTION

The present invention has been accomplished in view of the above-mentioned cost and technical background, and it is an object of the present invention to provide a system and method for reducing scattering of the excitation light emitted from a plurality of biological organisms after it is scanned by a beam of light.

This invention provides a system and method that allows for time-resolved fluorescent imaging of fluorescent samples. The user is able to receive temporally filtered pictures of the sample with a reduced amount of the scattered excitation light and the short lived background fluorescence. The system allows for adjustment of fluorescent gating time and delay time.

BRIEF DESCRIPTION OF SEVERAL VIEWS OF THE DRAWINGS

These and other advantages of the present invention will become more apparent as the following description is read in conjunction with the accompanying drawings.

FIG. 9 is a flow-chart that shows an example of how the system of FIG. 1 is implemented in accordance with the invention.

FIGS. 10A-10D depicts a graphical representation of simulated time-dependent fluorescent signals from any point in a sample. It is assumed that the fluorescence decays exponentially with a single lifetime $\tau$, excited by the passage of an Gaussian laser line of width w scanning the sample with speed v. System performance is determined by the unit less parameter $a=w/v\tau$. FIGS. 10A and 10B show the instantaneous fluorescence intensity where t' is the time elapsed since the passage of the excitation beam maximum. FIGS. 10C and 10D show the integrated signal yield as a function of the delay between excitation and start of detection.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1A:
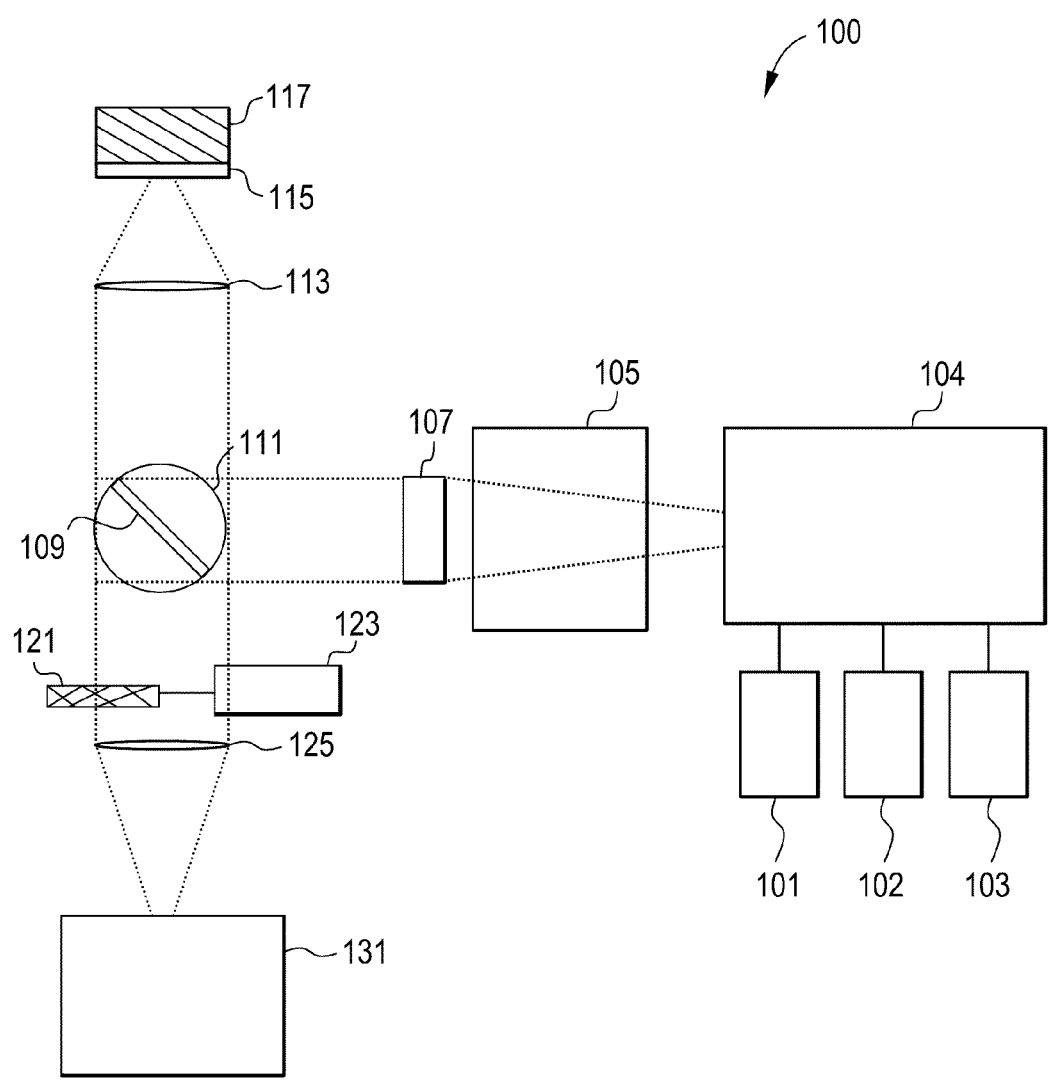
FIG. 1A illustrates a block diagram of a system in accordance with an embodiment of the invention.

A Time Resolved Fluorescent Imaging system or a Fluorescent Lifetime Imaging system 100 is schematically presented in FIG. 1A and includes one or more light sources 101, 102 and 103 to excite a fluorescent (or fluorescently stained or labeled) target 117 or sample 117 and one or more detectors 131 to detect fluorescent emissions. The system 100 may contain other components that will ordinarily be found in fluorescent microscopes, which will be described in more detail. For a number of the components there are multiple potential embodiments. In general, the preferred embodiments of the invention depend upon the target application. For the purpose of this document the preferred target application is a high throughput cellular screening device with the ability to image a wide range of fluorophores.

While the light sources 101, 102 and 103 can be any source capable of delivering light of the excitation wavelength to the target 117 or sample 117, preferably one or more excitation lasers are incorporated into the system 100. The light sources 101, 102, 103 may also be a light emitting diode, a lamp or any type of lighting source known to those of ordinary skill in the art. In a preferred embodiment of the invention, there are one or more lasers covering the optical spectrum from the near IR to the near UV. The light from each of these lasers 101, 102 and 103 can be coupled to the rest of the optical train by either delivering the light as a free space beam having the appropriate diameter, direction and degree of collimation or via fiber optic light delivery system. In another preferred embodiment of the invention, each excitation laser 101, 102 or 103 operates in TEM00 mode, with M2<1.2, RMS noise 1 Hz to 10 MHz<0.5%, and with polarization in a defined state. Any number of lasers can be used for this invention.

Next, the excitation laser light from the light sources 101, 102 and 103 are delivered to a laser-selection module 104. This module 104 selects light from one of the lasers 101, 102 and 103 and directs it into a beam-shaping module 105, where light from other lasers are blocked.

Figure 1B:
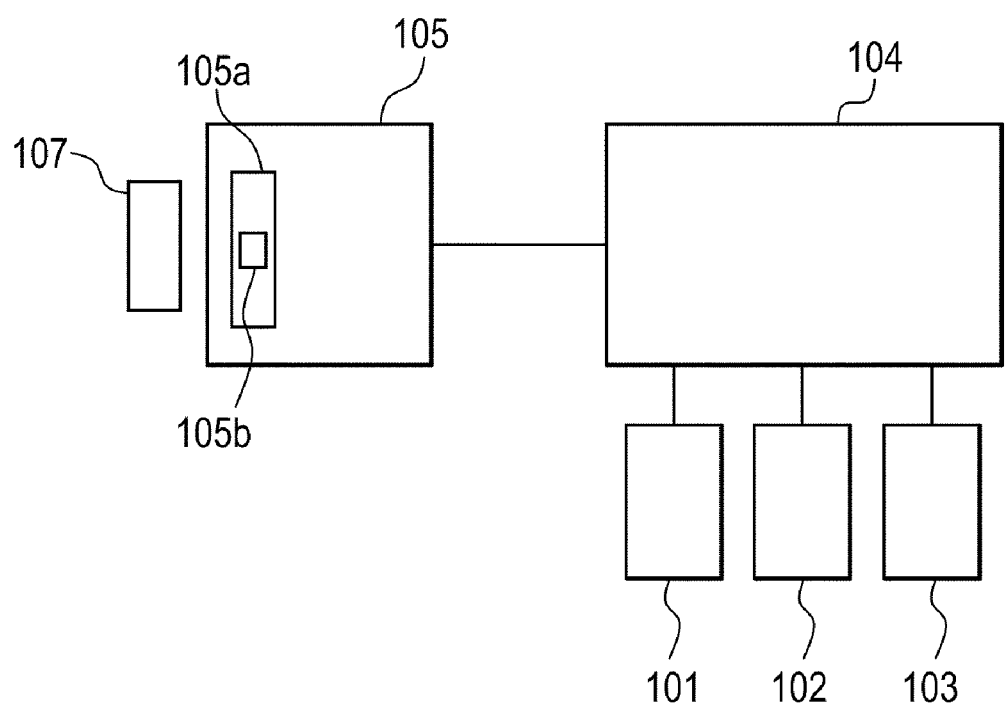
FIG. 1B depicts a beam expander of FIG. 1A with an adjustable light manipulation slit in accordance with an embodiment of the invention.

Excitation laser light from the light sources 101, 102 and 103 are preferably appropriately shaped by a beam shaper 105. Possible embodiments of the beam shaper 105 include, but are not limited to a laser beam-expander. In a preferred embodiment of the invention, the beam-expander 105 is used and its optical elements are corrected for chromatic aberration so as to minimize adjustment to the focus of the laser selection module 104 when switching between lasers 101, 102 and 103. The diameter of the laser beam is preferentially expanded to a Gaussian width a 1/e2 diameter be equal to that of the rear pupil of an objective 113. In a preferred embodiment of the invention, as shown in FIG. 1B the beam expander 105 includes an adjustable light manipulation slit 105a that is positioned at the focus point of the beam expander 105, where this light manipulation slit 105a has an opening 105b in the range of 1-20 µm. Preferably, the light manipulation slit 105a has an opening 105b of 10 µm or less, thereby enabling access to small values of the width of the beam 501 or a detection gate discussed in FIG. 5. Further, the light manipulation slit may have 1, 2, 3 or over 100 openings to manipulate the light emitted from the laser sources 101, 102 or 103. The adjustable light manipulation slit 105a may be made of metal, plastic or any material known to those of ordinary skill in the art. In another embodiment of the invention, the light manipulation slit 105a may be electrically or wirelessly connected to a control device (not shown) in the microscope system 100, which enables a person to close the opening 105b of the light manipulation slit 105a or remove the slit 105a.

In alternative embodiments of the invention, the type of beam-expander 105 (FIG. 1A) employed will depend upon the specific application and can include an anamorphic prism followed by a laser beam-expander without any beam shaper, and a chromatic aberration-free mirror-based beam expander.

In a TRF imaging mode, the excitation laser light passes through a line-forming element 107 that converts the collimated beam of laser light into a focused beam diverging in one direction only. The full divergence angle of the output beams $\Delta\theta$ may be given by:

$$\Delta\theta = 2*\arctan(D/(2*f)) \quad (1)$$

where f is the focal length of the objective 113, and D is the linear dimension of the imaging area on the target 117 in the direction perpendicular to the plane of FIG. 1.

In preferred embodiments of the invention, the line-forming element 107 includes, but is not limited to, a Powell lens (as described U.S. Pat. No. 4,826,299, incorporated herein by reference). The shape of the second conic-cylindrical surface is preferably specified to achieve both uniform illumination to within 10% over the range $\Delta\theta$ and more than 80% transmission of the laser light through the objective 113. Alternative preferred embodiments of the line forming elements 107, such as plano-convex cylindrical lenses, diffraction gratings, and holographic elements may also be used.

Next to the line forming element 107 is a scanning mirror 109 or scanning device. The scanning mirror 109 provides the scanning of the excitation light in the focal plane of the objective across the field of view of the microscope system 100. Scanning mirror 109 is located under the objective lens 113, this scanning mirror 109 operates as a typical scanning mirror or strip mirror that is able to receive the light or excitation light from the light sources 101, 102 and 103, then transfer the light through the objective lens 113 to cause the TRF agents in the sample 117 to emit fluorescent light or illumination light that is transmitted back through the objective lens 113 and around the scanning mirror 109 to an optical detector 131. Also, the scanning mirror 109 may be aluminum coated.

The excitation laser light is preferably reflected by the scanning mirror 109 that can be tilted about an axis vertical to the plane of FIG. 1. The angle of the tilt is set by an actuator 111. The mirror 109 may optionally include a narrow mirror centered on, or axially offset from, the rear of the objective 113. This is a preferred embodiment, and has a preferred geometry and reflective property as follows:

Width~1/10 times the diameter of the rear aperture of the objective.
Length~1.6 times the diameter of the rear aperture of the objective.
Optically flat.
Highly reflective $\lambda$/4-300 nm to $\lambda$/10-800 nm.

Figure 2:
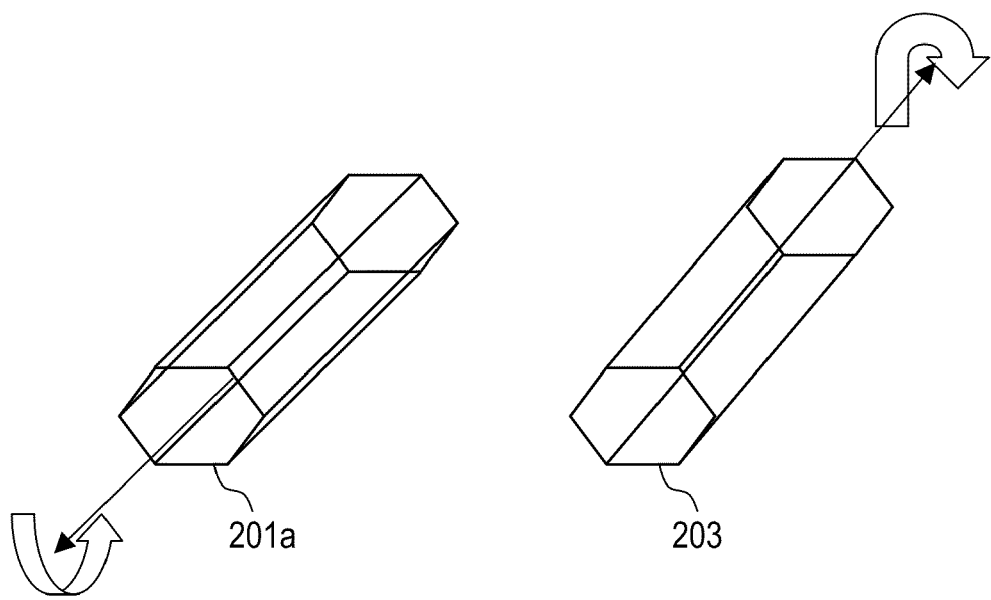
FIG. 2 shows several embodiments of the scanning mirror of FIG. 1 in accordance with one embodiment of the invention.

In another embodiment of the invention, as shown in FIG. 2 scanning mirror 109 may have any type of polygonal shape 201a, such as a pentagon, hexagon, or polygon with 5 to n faces that is motor driven. The scanning mirror 109 may also have any polygonal shape 203, such as a hexagon that is motor driven by the control device (not shown) of the microscope system 100, where the mirror 203 rotates with controllable speeds from 0.1 to 10,000 round per minute.

The actuator 111 may be a galvanometer with an integral sensor for detecting the angular position. This galvanometer 111 is driven by a suitably-tuned servo system. The bearing system is based on flexures to effectively eliminate wear and tear issues with friction in the bearing. The microscope objective 113 is above the actuator 111, where the excitation laser light from lasers 101, 102 or 103 passes through the objective 113. For the preferred embodiment of this objective 113, this objective 113 is:

highly corrected for geometric and chromatic aberrations over the desired field of view.
Has good flatness of field.
Transmits light from the near UV to the near IR.
Has the highest practical Numerical Aperture in order to achieve the best practical optical resolution and in order to collect as much of the fluorescence emission as practical.
Includes provision for correcting for the spherical aberration introduced by the sample-to-sample variation in the optical thickness of the sample support).

The time resolution of the system is limited by several factors. One factor is the time any point of sample 117 is exposed to the excitation light. For a laser line of width w (FIG. 5), scanning over the sample 117 with velocity v, any point of the sample 117 is exposed to the excitation for a duration of about w/v. The lowest value of w is that allowed by diffraction limited optics, of the order of 1 μm. Scanning speeds less than 1 m/s over the sample are easily achievable. Under these conditions each point in sample 117 is exposed to excitation for about 1 μs or more, allowing measurement of fluorescence lifetimes greater than 1 μs. For this invention, TRF reagents with lifetimes of 1 μs or longer are better suited to be measured than dyes with ns fluorescent lifetimes. When shorter fluorescence lifetime measurement is required, the speed of the scanning mirror 109 needs to be increased and a preferred option is to use polygonal mirror scans, examples of which are shown in FIG. 2. At high scanning speeds system capability may become limited by several factors expounded on in the text below.

In a preferred operation of this invention, the excitation laser light passes through a transparent optical material 115 that supports the sample 117. The thickness, curvature and optical properties of this supporting material may vary from sample-to-sample. Ideally there is minimal curvature. The excitation laser light is incident on the sample 117. The sample 117 may be live biological organisms, biological cells, bacteria, chemical and or biochemical reagents, synthetic and or natural materials, on a slide, in wells of a micro titer plate, or any other convenient sample holder. When the system 100 is properly focused the sample 117 has an illumination area that is illuminated by a line of laser light from light sources 101, 102 or 103. Fluorescent material in the sample emits fluorescent light as a result of illumination by the line of light.

The fluorescent light emitted from through the sample 117 and is collected by the objective 113. The fluorescent light passes through or by the mirror 109 depending upon the embodiment of the mirror.

Next, the fluorescent light passes through a suitable optical filter 121 that efficiently transmits the fluorescent light and blocks the wavelength of the excitation laser. The filter 121 may be optionally tilted about an axis perpendicular, using a device 123, to the plane of FIG. 1A so that reflections from the filter are outside of the field of view of the camera 131.

In a preferred embodiment the filter 121 will not obscure the fluorescence emission. The fluorescent light passes through the image-forming lens 125 or tube lens 125. In a preferred embodiment of the invention: The geometrical distortion of the lens is very low (<0.2%) across the region imaged by the camera 131. Also, the lens is corrected for all other geometrical and chromatic aberrations.

The optical detector 131 is preferably a CMOS and/or CCD detector which is capable of detecting the fluorescent light and generating an image. In preferred embodiments of the invention, the detector 131 is capable of an independent reset and readout of pixels (random access feature) and acquiring signal by random access scanning In a preferred embodiment of the invention, the fluorescent emission is focused onto a CMOS detector 131 having a rolling shutter (also known as a focal-plane shutter). In a line scan mode, the detector 131 with a rolling shutter acquires images in "stripes" of pixels. The "length" of the stripes is aligned perpendicular to the plane of FIG. 1. For a description of the operation of this type of camera, please refer to the Application Note MTD/PS-0259 Shutter Operations for CCD and CMOS Image sensors published by Eastman Kodak Company, incorporated herein by reference.

The detector 131 is preferably a CMOS detector that includes a rectangular array of light-sensitive square pixels organized in rows and columns where data is read column-by-column. This feature allows for virtual movement of the detection area or virtual detection region, synchronized or shifted to be placed behind the image of the excitation area or illumination area on the sample 117. In the line scan mode, the laser is focused to a uniformly illuminated line oriented parallel to the columns of the CMOS detector 131. This line moves as the rolling shutter moves across the camera. In this way the fluorescence emission generated by the line of illumination is collected by the sensor.

Detector 131 is electrically or wirelessly connected by a communication link to a computer 112. The computer 112 may be referred to as an image receiving device 112 or a high throughput screening device. In another embodiment of the invention, image receiving device 112 may be located inside of the image transmitting device 100. The image receiving device 112 acts as a typical computer, which is capable of receiving an image of the sample 117 from the optical detector 131, then the image receiving device 112 is able to build up or reconstruct images by utilizing a standard image processing software program, algorithm or equation usually one pixel at a time. Also, the computer 112 may be a personal digital assistant (PDA), laptop computer, notebook computer, mobile telephone, hard-drive based device or any device that can receive, send and store information through the communication link 131. Although, one computer is utilized in this invention a plurality of computers may be utilized in place of computer 112.

Figure 3:
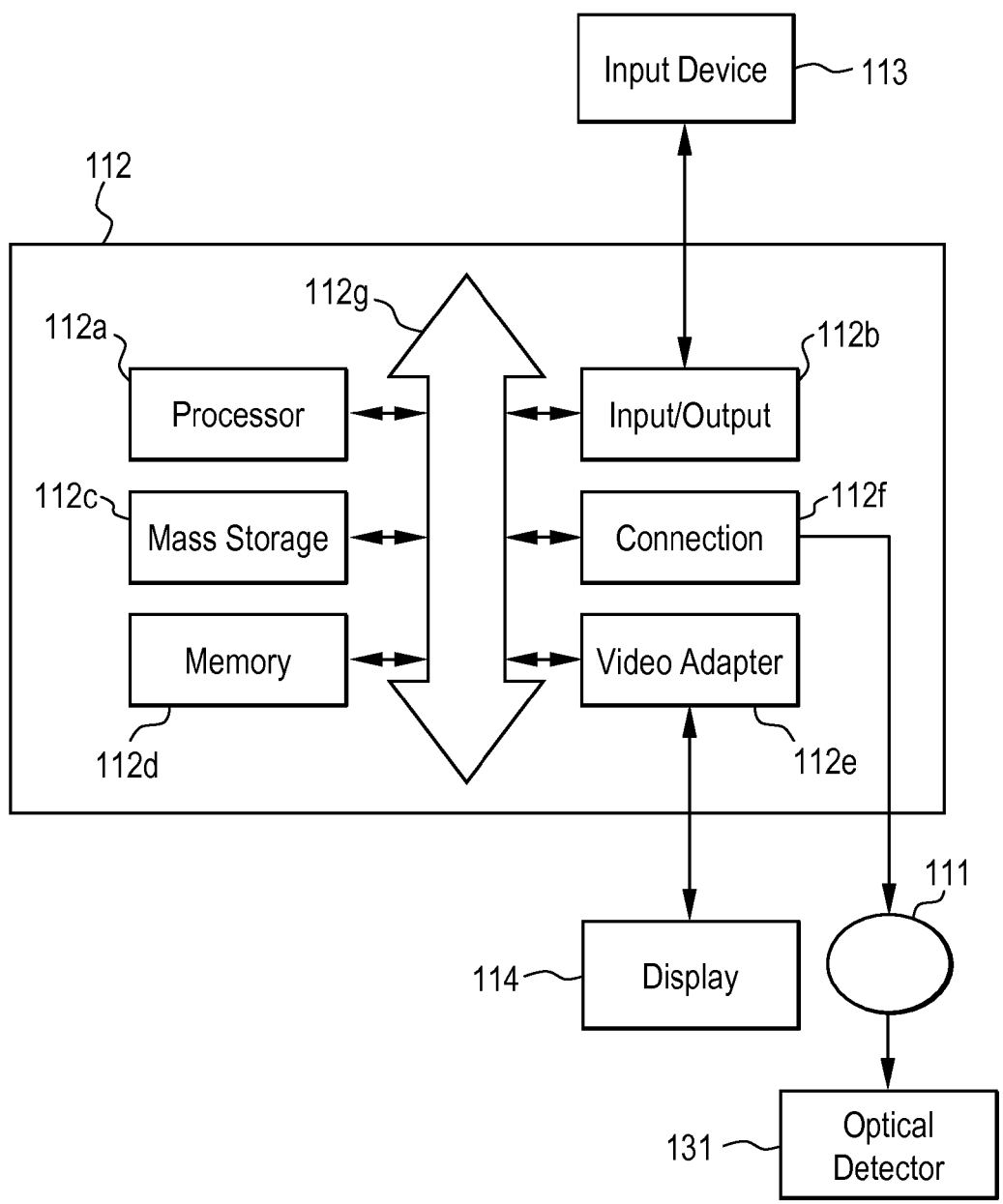
FIG. 3 is a schematic diagram of an image receiving device of the system of FIG. 1 in accordance with the invention.

FIG. 3 illustrates a schematic diagram of the image receiving device of the system of FIG. 1. Imaging receiving device 112 includes the typical components associated with a conventional computer. The imaging receiving device 112 includes: a processor 112a, an input/output (I/O) controller 112b, a mass storage 112c, a memory 112d, a video adapter 112e, a connection interface 112f and a system bus 112g that operatively, electrically or wirelessly, couples the aforementioned systems components to the processor 112a. The processor 112a may be referred to as a processing unit, a central processing unit (CPU), a plurality of processing units or a parallel processing unit. System bus 112g may be a typical bus associated with a conventional computer. Memory 112d includes a read only memory (ROM) and a random access memory (RAM). ROM includes a typical input/output system including basic routines, which assists in transferring information between components of the computer during start-up.

Above the memory 112d is the mass storage 112c, which includes: 1. a hard disk drive component (not shown) for reading from and writing to a hard disk and a hard disk drive interface (not shown), 2. a magnetic disk drive (not shown) and a hard disk drive interface (not shown) and 3. an optical disk drive (not shown) for reading from or writing to a removable optical disk such as a CD-ROM or other optical media and an optical disk drive interface (not shown). The aforementioned drives and their associated computer readable media provide non-volatile storage of computer-readable instructions, data structures, program modules and other data for the computer 112. Also, the aforementioned drives include the scanning algorithm, software or equation described herein to obtain an acceptable average signal level, which will be described in the flow chart of FIG. 9 that works with the processor 112 that has a technical effect of generating a graphical representation of the signal level for a plurality of time instances of the sample 117 related to fluorescence intensity. In another embodiment, the scanning algorithm, software or equation may be stored in the processor 112a, memory 112d or any other part of the image receiving device 112 known to those of ordinary skill in the art. In a preferred embodiment of the system where faster data processing may be needed, mathematical operations for integration of intensity and or calculation of mean lifetime at each pixel position are performed on-chip on a specially designed CMOS chip at the site of detector 131 as described in the reference (E1 Gama A and Eltoukhy H, "CMOS image sensors," *IEEE Circuits & Devices* 21, 6-20 (2005); Bigas M, Cabruja E, et al., "Review of CMOS image sensors," *Microelectronics J* 37, 433-451 (2006)), which is hereby incorporated by reference).

Input/output controller 112b is connected to the processor 112a by the bus 112g, where the input/output controller 112b acts as a serial port interface that allows a user to enter commands and information into the computer through input device 113, such as a keyboard and pointing devices. The typical pointing devices utilized are joysticks, mouse, game pads or the like. A display 114 is electrically or wirelessly connected to the system bus 112g by the video adapter 112e. Display 114 may be a typical computer monitor, Liquid Crystal Display, High-Definition TV (HDTV), projection screen or a device capable of displaying characters and/or still images generated by a computer 112. Next to the video adapter 112e of the computer 112, is the connection interface 112f. The connection interface 112f may be referred to as a network interface which is connected, as described above, by the communication link to the optical detector 131. Also, the image receiving device 112 may include a network adapter or a modem, which enables the image receiving device 112 to be coupled to other computers.

Figure 4:
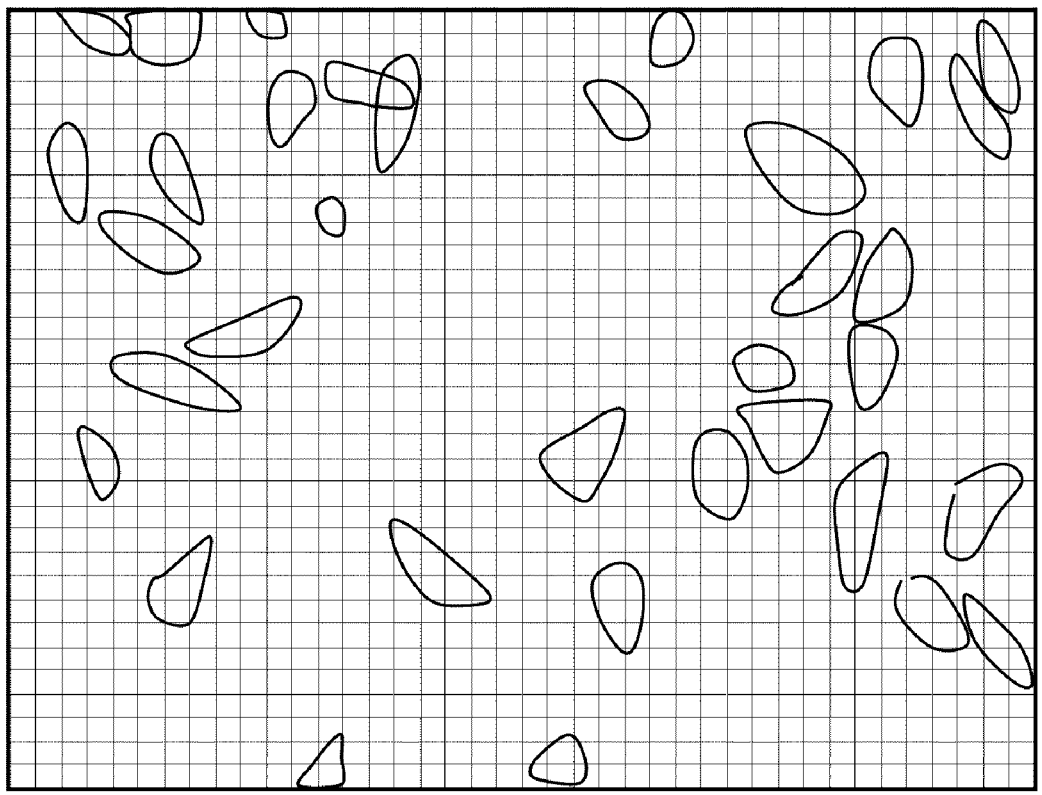
FIG. 4 is a graphical representation of the image of the field of view (FOV) of the plurality of biological organisms in accordance with the invention.

FIG. 4 is a graphical representation of addressable pixel areas of the optical detector 131, showing the image of a grouping or plurality of biological organisms. The actual number of pixels is normally much higher, numbering into the millions. This representation illustrates the image of sample 117, which is placed on the object stage of the microscope system 100.

Figure 5:
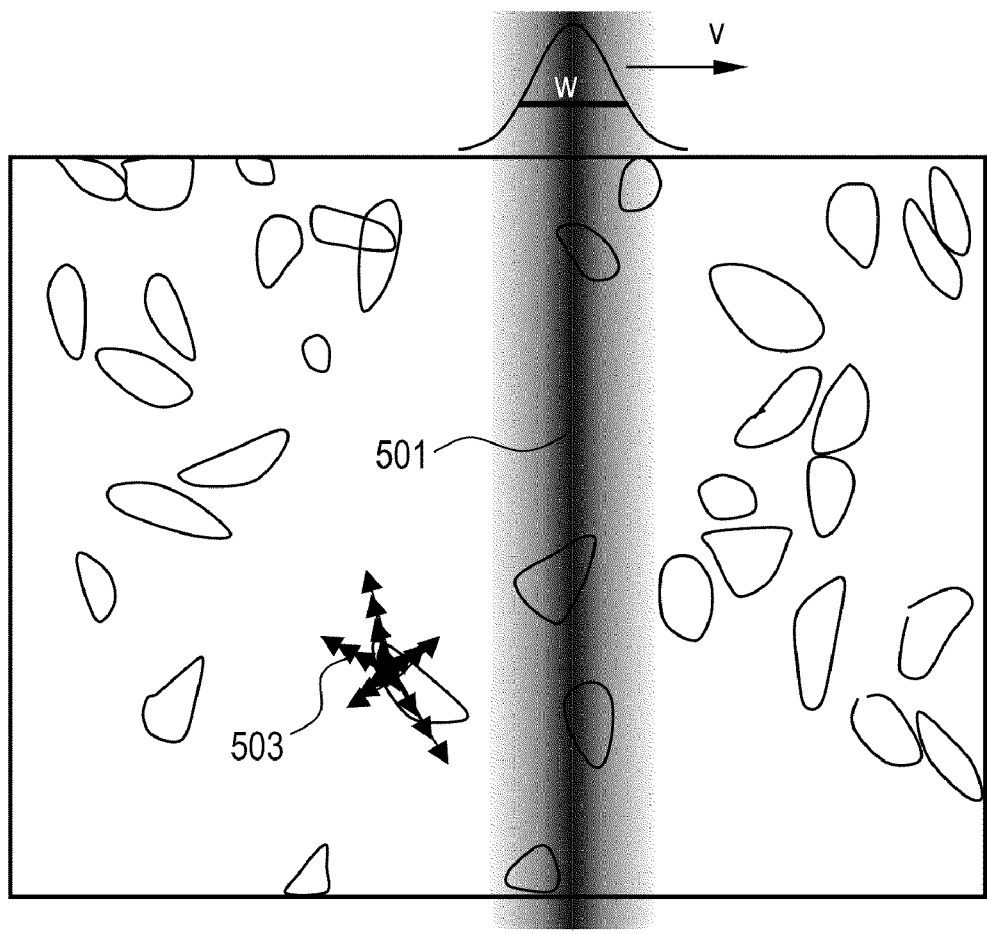
FIG. 5 depicts an example of the graphical representation of FIG. 4 at the sample 117, where the plurality of biological organisms is scanned by a beam in accordance with the invention.
Figure 6:
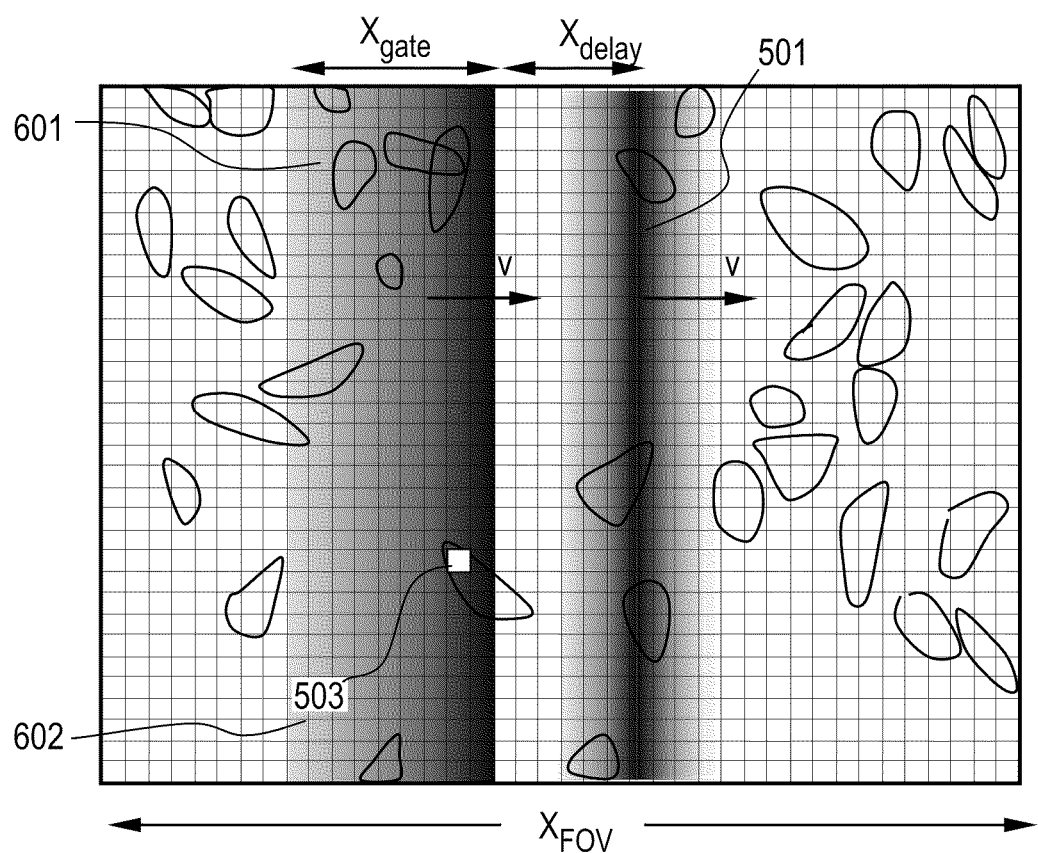
FIG. 6 depicts the graphical representation of the image of the sample in FIG. 5 in accordance with the invention.

FIG. 5 is a graphical representation of an example of the field of view (FOV) of the sample that generates the example image of FIG. 4 on the detector 131, where the plurality of biological organisms are scanned by at least one beam from the light source. FIG. 6 shows the system employing laser line scanning, but as discussed above, in other embodiments point scanning of the sample may also be employed. In particular, at least one beam 501 from the light source 101 is scanned over the plurality of biological organisms in sample 117. For this example, only at least one particular point 503 in the plurality of biological organisms of the sample 117 is examined. However, a plurality of points in the plurality of biological organisms of the sample 117 may be scanned by at least one beam 501. This point 503 is represented by x and y coordinates of the sample 117 on an object stage of the microscope system 100. The sample point 503 experiences the excitation light for a duration of about w/v, where w is the width of the profile of the focused excitation beam 501 from light source 101 and v is its velocity of scanning on the sample 117. Excitation beam 501 may be referred to as an excitation light or excitation region. This excitation region 501 is any place in sample 117, such as point 501 where a portion of the sample 117 will become excited and emit fluorescence after the point 501 has been scanned by a beam of light from light source 101. The excitation region 501 has a shape in the form of a point, line or a rectangle.

Subsequent to the passage of the light source 101 over the plurality of biological organisms of the sample 117, the plurality of excited fluorescent probes in the biological organisms emit light for a certain period of time. The period for emission of light from sample point 503 of sample 119 is characterized by the probe's mean emission lifetime at that location, and is referred to by the symbol τ.

Figure 7:
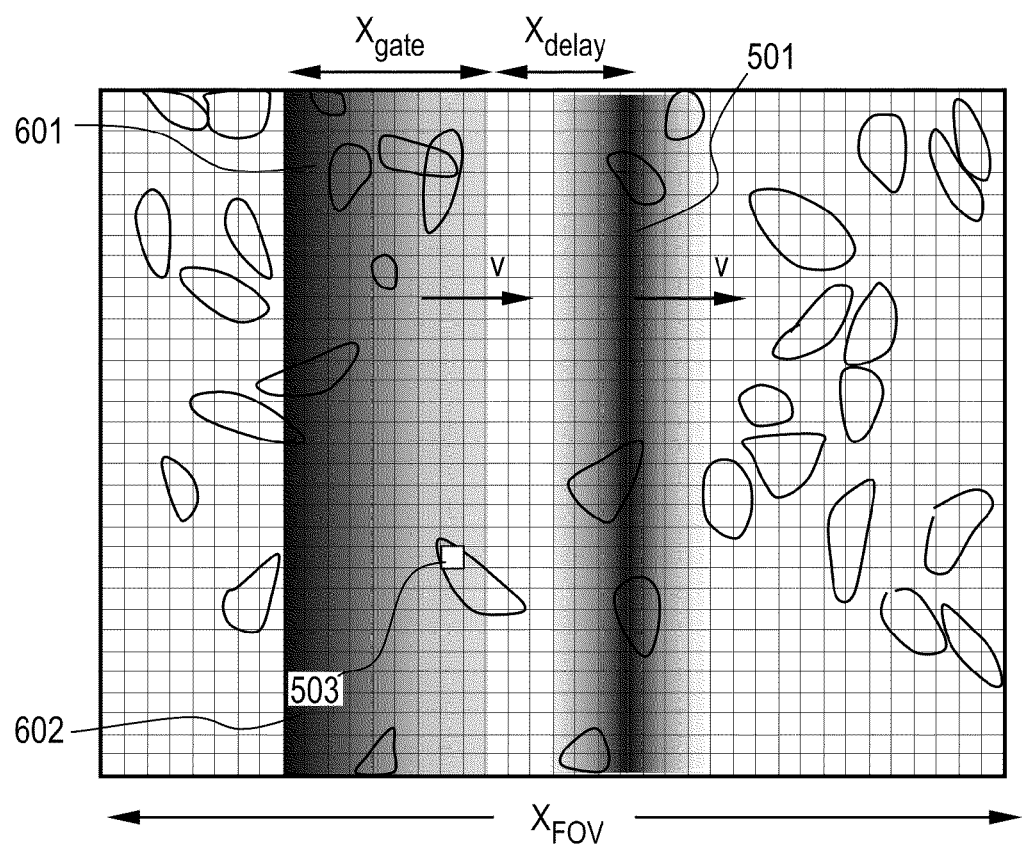
FIG. 7 depicts another graphical representation of the image of the sample in FIG. 5 in accordance with the invention.
Figure 8:
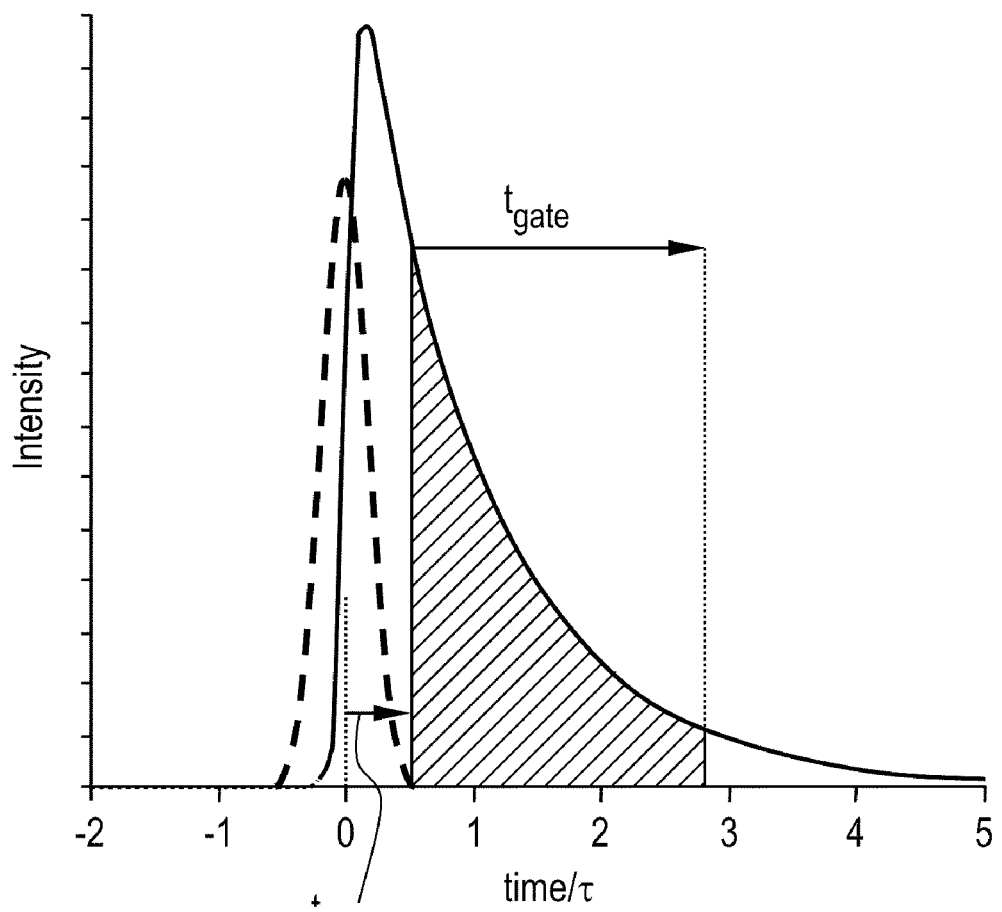
FIG. 8 solid trace depicts an example graphical representation of the instantaneous fluorescence intensity signal vs. time generated by the pixel 503 in FIG. 6, in accordance with the invention. The dashed profile represents the excitation intensity experienced by point 503 as a Gaussian shaped laser line scans over it.

FIG. 6 illustrates a graphical representation of the instantaneous fluorescence intensity arriving at the detector in the time-resolved fluorescence intensity detection (TRF) modality. Instantaneous intensity is represented by graphical shading. In the TRF mode, the value of each image pixel will be proportional to the integrated fluorescence intensity at the corresponding sample position, integrated for the duration of the gating window. The corresponding time profile of the fluorescence intensity detected by sample point 503 is represented in FIG. 8. The graphical representation of FIG. 6 is an image of the FOV of sample 117 shown in FIG. 5, where light is radiated by the plurality of biological organisms in response to excitation by the beam 501. In a preferred embodiment, area 601 is an active pixel area, as found in CMOS detectors, corresponding to the sample area that radiates emission under the influence of the beam from light source 101 that earlier passed over it. Active pixel area means that the detector 131 pixels in this area of the sample 117 are active in detection of photons by the biological materials in sample 117 and generation of photoelectrons. The active pixel area is programmed to move at the same speed v as that of the image of beam 501 from light source 101. Pixel areas closer in distance from beam 501 image are also closer to it in time. As a result areas farther behind from excitation beam 501 have had more time for emission to decay and have dimmer fluorescence signals than areas closer to the beam. In FIG. 7 the shading shown in detection region 601 is meant to represent the instantaneous fluorescence intensity arriving at the detector. For depiction simplicity all sample areas are assumed equally fluorescent. Pixels nearer to the excitation area 501 see more fluorescence intensity because less time has passed since the excitation area moved over those points. Pixels in the immediate vicinity of the image of the excitation area 501 are set to be inactive and as a result the two major contributors to fluorescence background, scattered excitation light and short-lived auto-fluorescence, are not detected. In this way time and distance are related by (distance)=(velocity)·(time), where both distance and scanning velocity refer to measures on the sample object plane, and not the image plane at the detector, where both distance and velocity are magnified by the system's optical magnification. By the same relation, a distance ($X_{delay}$) from the starting edge of the active pixel area to the peak of excitation area 501 corresponds to a delay time ($t_{delay}$) between excitation and start of detection, given by, $t_{delay}=X_{delay}/v$.

FIG. 7 illustrates the same graphical representation as in FIG. 6, but the shading in detection area 601 is meant to represent the time-integrated photoelectrons at each pixel. The integrated photo electrons in each pixel of the active area are higher in pixels farther away from excitation line 501. For pixel 503, the integrated signal intensity corresponds to the dashed area in the gating window of FIG. 8. Readout of the integrated TRF data is programmed to take place from the column of pixels 602 (the trailing edge column of detection area 601), where each pixel has been exposed for the gating time duration $t_{gate}=X_{gate}/v$. As discussed below, depending on the speed of scanning and the clock speed of the CMOS detector, two different types of detector architecture may be needed.

The solid trace in FIG. 8 shows an example of the instantaneous photoelectron generation of the pixel 503, vs. time, corresponding to the fluorescence intensity of sample point 503, vs. time. The dashed profile represents the excitation intensity experienced by point 503 as a Gaussian shaped laser line scans over it. At time 'zero,' the peak of the excitation area 501 passes over the sample point 503. The delay time is the time elapsed from the moment of the passage of the peak of excitation beam 501 over point 503, to the time pixel 503 is set active to detect and generate photoelectrons. The delay time can be set to be greater than 1 w/v, preferably set to about 2 w/v. The length of the active pixel area (in the direction of motion) constitutes the gating distance ($X_{gate}$), with the measurement gating time of FIG. 7 given by, $t_{gate}=X_{gate}/v$.

Two timing requirements expounded on below set preferable upper and lower limits to the scanning velocity v. Between the two limits, higher scanning speeds are preferable because faster averaging and data acquisition are enabled. However, very fast scanning may also require more expensive cameras with giga hertz clock speeds (see below). These requirements are meant to be illustrative rather than limiting the scope of the invention. For the TRF modality, gating times can be chosen from near zero (1 pixel width distance, FIG. 7) to several lifetimes, preferably to about 3τ. In this way full integration of the emitted light is made possible (FIG. 8). To avoid the overlap of the excitation and detection regions, the delay time should be set to greater than 1 w/v, preferably set to about 2 w/v, that is 2 w/v<τ (FIG. 6), leading to a preferable lower limit to the scanning velocity, given by v>2 w/τ.

The dose of excitation light received by any point 503 and the signal generated by the point per scan is higher with slow laser scanning speeds. However, for two reasons its preferable to employ higher scanning speeds and average the resulting multiple image frames into a single final image: (1) Over multiple scanning the mean dose of excitation light received by any point in the sample becomes independent of the scanning speed; (2) high doses of focused excitation light may lead to significant sample ground state depopulation, particularly for long lived TRF reagents, with consequent loss of signal efficiency and potential sample photobleaching.

At extremely high scanning speeds the excited sample will not have time to decay during the scan of the field of view. Consequently, the gating distance $X_{gate}=v·t_{gate}$ (FIGS. 7-8) may need to become larger than the field of view (that is $X_{gate}>X_{FOV}$). A large gating distance implies a long reading time. Although this setting is possible with CMOS rolling shutters it is not a preferred condition because in this case re-scanning should be avoided until the emission from the previous scan is died down. As a result this mode of operation increases the dead time between scans with consequent loss of efficiency in usage of excitation light. Consequently, it is preferable to have a gating distance smaller than the field of view (that is $X_{gate}<X_{FOV}$). Given the previously stated preference for gating time about 3τ, this requirement sets a preferable upper limit to the scanning velocity, given by $v<X_{FOV}/3τ$. The two preferred scanning speed requirements can be summarized as $X_{FOV}/3τ>v>2$ w/τ. However, the foregoing requirements should be considered illustrative rather than limiting the scope of the invention.

As an example, for microscopic imaging under a 10× magnification objective, where the field of view is about $X_{FOV}$=0.5 mm over the sample (5 mm over the CMOS chip with 1000×1000 pixels, or $X_{FOV}$=1000 pixels), one can focus a laser line to near diffraction limit with a width w≈1 μm (10 μm image width over the CMOS, or w=2 pixels). One can calculate that for TRF reagents, with mean fluorescence lifetime τ of about 1 ms, the required scanning velocity v is preferably set to within 0.2 to 16 cm/s over the sample (4 to 330 pixels/ms over the chip). Such speeds require camera clock speeds of about 4 to 330 MHz (see below). For a lifetime of 0.1 ms the required scanning velocities and camera readout speeds will be 10 times higher. The lower range of clock speed is easily satisfied by commercially available CMOS cameras.

Another timing condition for the TRF imaging of FIGS. 6 and 7 is that the speed of pixel readout from the detector column 602 should match the speed of scanning The pixel readout rate depends on a number of factors: the clock speed of the detector 131, the speed of scanning, the number of pixels within the detection area, the choice of the modality of time resolved detection, FLIM vs. TRF, and whether the mathematical processing of data takes place on the charge collected in each pixel on chip or after readout (El Gamal A and Eltoukhy H, "CMOS image sensors," *IEEE Circuits & Devices* 21, 6-20 (2005); Bigas M, Cabruja E, et al., "Review of CMOS image sensors," *Microelectronics J* 37, 433-451 (2006)). Currently the clock speed of CMOS detectors ranges from about 10 GHz for a research grade detector to about 30 MHz for commercial grade detectors.

As an example, for the TRF imaging example considered above, with a lifetime of 1 ms, about 1000 detector columns are to be read at the speed of 4 columns to 330 columns per ms. Because each column has about 1000 pixels, this requires a camera clock speed of 4 to 330 MHz (depending on the choice of scanning velocity). For a lifetime of 0.1 ms the required scanning velocities will be 10 times higher and camera readout speeds need to be 40 MHz to 3 GHz. The lower speeds are in the range of commercial grade detectors but the higher speeds require specialized CMOS detectors.

In a preferred embodiment, a considerable relaxation in readout speed requirement can be implemented by usage of specially designed CMOS detectors with on-chip data processing capability. For example, corresponding for each detection pixel there can be an on-chip integration where the detected charge is registered to. In this case, no data readout takes place until the full area is scanned. Then, while the scanning mirror resets for its second run, the registered elements are readout at normal speeds. In another preferred approach, the CMOS is programmed to perform on-chip integration of the multiple scans of the sample until a satisfactory signal level is achieved. There is only one normal frame readout post the multiple scanning operation.

For a fluorescence lifetime imaging (FLIM) operation each image pixel value will represent the mean fluorescence lifetime ($\tau$) of the sample at that location. $\tau$ is preferably evaluated on-chip by specially designed data processing elements associated with each light sensing pixel. A variety of algorithmic approaches known to experts in the art can be implemented. A simple approach evaluates the mean lifetime from $$\tau = \sum_{i=0}^{\infty} t_i I(t_i) \Big/ \sum_{i=0}^{\infty} I(t_i), \quad [1]$$

where in eq. [1], for any given pixel 503 (FIG. 6): time $t_0=0$ starts when the leading edge of the active pixel area 601 reaches the pixel 503, and its subsequent values ($t_1$, $t_2$, $t_3$, ... ) are calculated from the distance of pixel 503 from the leading edge of active pixel area 601 divided by scanning velocity v; $I(t_i)$ is the instantaneous charge generated at the light sensing pixel at time point $t_i$;

$$\sum_{i=0}^{\infty} I(t_i)$$

is the accumulated charge transferred to an integrating registry element; The sum $$\sum_{i=0}^{\infty} t_i I(t_i)$$

is evaluated in a separate on-chip element associated with each light sensing pixel. The infinity symbol ($\infty$) is meant to represent a sufficiently long user chosen time, longer than $2\tau$, preferably about $3\tau$. The CMOS is programmed to perform on-chip summation of the multiple scans of the sample until satisfactory signal levels are achieved for both $$\sum_{i=0}^{\infty} I(t_i) \text{ and } \sum_{i=0}^{\infty} t_i I(t_i).$$

There are only two normal frame readouts of the two signals post the multiple scanning operation. After the readout, the value from $$\sum_{i=0}^{\infty} I(t_i)$$

for each pixel constitutes the signal of the TRF image, while the value calculated from Eq. [1] constitutes the FLIM image.

FIG. 9 is a flow-chart of an example of how the time-resolved imaging system of FIG. 1 is utilized. In order to initiate the measurement process, at block 900 a user inserts a sample 117 labeled with appropriate time-resolved fluorescent (TRF) reagents onto the object stage of the microscope system 100. Based on a prior knowledge of probe lifetime $\tau$ (typically 0.1 to 1 ms for TRF reagents) and the clock speed capability of the CMOS chip, the user adjusts three input parameters the instrument needs: the scan velocity v is set, preferably so that it lies in the higher range preferably set by $X_{FOV}/3\tau > v > 2$ w/$\tau$, and allowed by camera clock speed, described in FIGS. 6-8; The delay time ($t_{delay}$) described in FIGS. 6-8, is set to a value greater than w/v, preferably to 2 w/v; The gate time ($t_{gate}$), described in FIGS. 6-8, is set to a value greater than $2\tau$, preferably to $3\tau$; The number of rescanning iterations (N) is set to a value such that a desired level of signal-to-noise ratio can be attained. Next the system starts the data acquisition.

At block 901, the system 100 utilizes the light source 101 of the microscope system 100 to scan a beam of light from light source 101 (FIGS. 5-7) over at least one point 503 in the plurality of biological organisms in the sample 117 and excite the light absorbing fluorescent probes (fluorescence) of point 503 (block 903) at an excitation area 501 or illumination area 501. In other words, the illumination area 501 is formed on the target 117 to excite fluorescence from at least one point on the target 117. At block 905 the fluorescent emission of point 503 is guided by the optical elements of system 100 to detector 131, preferably with individually addressable detection elements, such as a CMOS detector. At block 905 the detector is programmed to have or form a detection area 601 of width $X_{gate}=v\, t_{gate}$, (FIGS. 6-8) that virtually moves in unison or synchronization with the excitation area 501, but shifted in space and geometrically scaled behind it by $X_{delay}=v\, t_{delay}$, (FIGS. 6-8). The charge generated at the detector elements can be readout in two ways as shown in blocks 907 and 909. The geometrical scaling provides a relationship between a size of the illumination area and a size of the detection area with respect to a direction of moving the illumination area and the detection area, wherein the size of both the illumination area and the detection area in a direction perpendicular to the moving direction is the same and the size of the detection area in the moving direction is defined by a gating time. Further, the geometrical scale is a ratio between a size of the illumination area 501 and the detection area 601 along and across a moving direction of the illumination area 501 and the detection area 601 over the target 117. For example, if a width of an illumination area along a moving direction is equal to 1 micron then the width of the detection area 601 may be equal to 2 micron which means the geometrical scaling at a factor of 2. If the width of the illumination area 501 in a direction perpendicular to moving is 0.5 mm the corresponding with of the detection area 601 may also be 0.5 mm so the geometrical scaling has a factor of 1.

In block 907 the charge integrated in the trailing column of the detection area 601 (FIGS. 6-7, column 602) is readout directly into processor 112a at the same speed the detector pixels are scanned. In this case, the processor 112a must carry out the averaging of results from the multiple (N) scans of the sample. Next, at block 911, the computer 112 utilizes processor 112a to determine or count if the rescanning iterations (N) has been reached to determine if another scan of the at least one point 503 in sample 117 has to take place. If the number of rescanning iterations (N), for example 100 scans, has not been reached, then another scan is generated and the process begins at the start block. If the number or rescanning iterations (N), for example 100 scans, has been reached, then another scan is not generated and the process continues to block 913. At block 913, an image representation is produced on the display 114 based on the data accumulated by the processor 112a that illustrates a highly fluorescent image representation or picture of the point 503 that has little background scattered light.

At block 909, in a preferable embodiment of the invention the mathematical processing of the data takes place as in Equation 1, discussed above on the on-chip processor, on the detection chip of the CMOS detector 131. In this case, the chip can detect and process the fluorescence of all N scans of the at least one point 503 of the sample 117 to generate final values of the integrated intensity and or mean lifetime that are readout directly. Next, at block 911, the microscope system 100 utilizes the CMOS detector 131 with the detection chip to determine or count if the rescanning iterations (N) has been reached to determine if another scan of the at least one point 503 in sample 117 has to take place. If the number of rescanning iterations (N), for example 100 scans, has not been reached, then another scan is generated and the process begins at the start block. If the number or rescanning iterations (N), for example 100 scans, has been reached, then another scan is not generated and the process continues to block 913. At block 913, an image representation is produced based on the data accumulated by the CMOS detector 131 with a detection chip that illustrates a highly fluorescent image presentation or picture of the point 503 that has little background scattered light and or also to generate a lifetime image (FLIM) where each pixel value represents the mean lifetime of sample fluorescence, calculated by the processor 112a according to eq. [1] above.

Figure 10A:
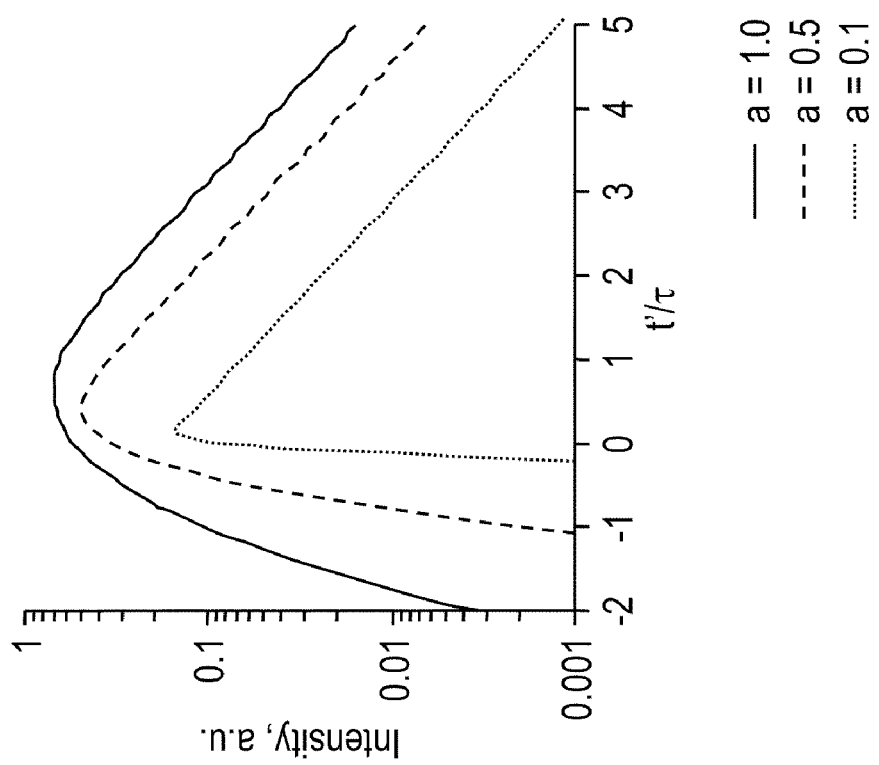
Figure 10B:
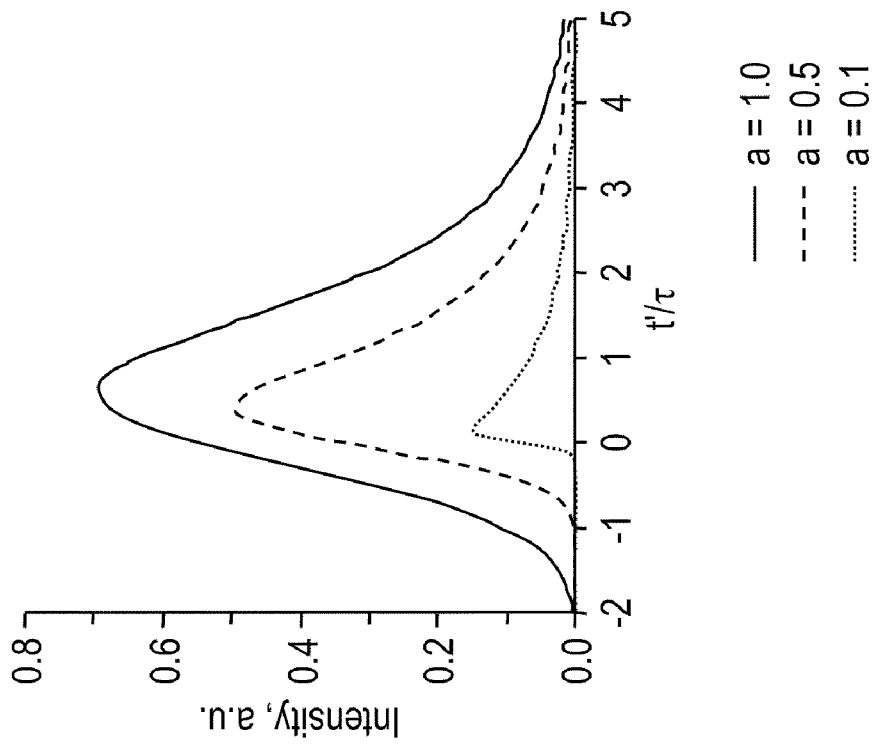

FIGS. 10A and 10B show examples of calculated fluorescence intensity vs. time profiles, modeled for a sample point 503 with lifetime $\tau$ (FIG. 5), illuminated with an Gaussian-profile excitation beam 501, having a width w. The unitless parameter $a=w/v\tau$ determines the form of the intensity profiles. The calculation results are shown for a=1, 0.5 and 0.1. These results pertain to low power excitation levels where saturation effects are not encountered. t' describes the time elapsed since the peak of excitation passed over point 503. The maximum of each profile is approximately in proportion to a. FIG. 10B shows the intensity plots in a logarithmic scale, demonstrating that the decays quickly become exponential when the beam has moved out of the vicinity of point 503, i.e. when, $t' \geq \tau_{ex}=w/v$. This justifies the earlier stated preference for having the delay time $t_{delay}$ greater than w/v, preferably $\geq 2$ w/v.

FIGS. 10C and 10D show plots of relative TRF yield (integrated photo electron yield) vs. delay time, calculated for a long gating time. The results show that high yields are obtained for small delay times. From this result and the previous the calculation justifies the preferred delay time of $t_{delay} \approx 2$ w/v.

This invention provides a system and method that allows for time-resolved fluorescent imaging of fluorescent samples. The user is able to receive temporally filtered pictures of the sample with a reduced amount of the scattered excitation light and the short lived background fluorescence. The system allows for adjustment of fluorescent gating time and delay time.

It is intended that the foregoing detailed description of the invention be regarded as illustrative rather than limiting and that it be understood that it is the following claims, including all equivalents, which are intended to define the scope of the invention.

What is claimed is:

1. An apparatus for time-resolved fluorescent microscopy comprising:
   at least one optical source that provides an excitation radiation configured to utilize at least one scanning device, wherein the at least one scanning device is configured to move the excitation radiation across an area of a target, wherein the target is configured to receive the excitation radiation and emit fluorescence from an illumination area on the target; and
   at least one detector configured to detect the fluorescence emitted from the target, wherein the at least one detector is capable of random access reading of said fluorescence emitted from the target, wherein the random access reading of said fluorescence emitted from the target provides a detection region that is configured to be geometrically scaled to be larger than the illumination area on the target and the scanning device is configured to move the illumination area, wherein the at least one detector is configured to move said detection region in synchronization with the illumination area of the target, wherein the detection region is shifted with respect to an image of the illumination area of the target.

2. The apparatus of claim 1, wherein the at least one optical source is selected from the group consisting of lasers, laser diodes, light emitting diodes, lamps, and combinations thereof.

3. The apparatus of claim 1, wherein the at least one detector includes one or more two dimensional pixel-based optical receivers capable of independent reset and readout of such pixels.

4. The apparatus of claim 3, wherein the at least one detector is selected from the group consisting of a CMOS detector, a CCD, PMT and a photodiode.

5. The apparatus of claim 1, wherein the at least one optical source includes a means to illuminate a single point on the target and further includes a means to scan the single point illumination across an imaging area of the target.

6. The apparatus of claim 1, further comprising a line forming means to illuminate a line portion of the target and further includes a means to scan the line portion illumination across an imaging area of the target.

7. The apparatus of claim 6, wherein the line forming means is selected from the group consisting of Powell lenses, cylindrical lenses, diffraction gratings, holographic elements and combinations thereof 8. The apparatus of claim 1, wherein the at least one scanning device is from the group consisting of one or more galvanometers and rotary polygonal mirror scanners.

9. The apparatus of claim 1, wherein the at least one detector is a CMOS detector which further comprises a rolling shutter means.

10. The apparatus of claim 9, wherein the rolling shutter means is configured to shift the detection region with respect to the image of the illumination area of the target.

11. The apparatus of claim 1, wherein the detection region has a width equal to a product of a velocity that the excitation radiation is moving across the target and a required gating time.

12. The apparatus of claim 1, wherein the at least one scanning device is configured to scan across the target a plurality of times.

13. The apparatus of claim 1, wherein the at least one detector is connected to a computer.

14. The apparatus of claim 13, wherein the computer is configured to read out the fluorescence emitted from the target as the target is scanned by the scanning device.

15. The apparatus of claim 14, wherein the computer is configured to average the results of the read out of the fluorescence emitted from the target.

16. The apparatus of claim 15, wherein the computer is configured to read out the fluorescence emitted from the target as the target is scanned by utilizing an ON chip processor, wherein the target has a fluorescent lifetime.

17. The apparatus of claim 13, wherein the computer includes a display, wherein the display is configured to display the data accumulated by the computer that illustrates a fluorescent representation of the illuminated target.

18. A method for time-resolved fluorescent imaging, comprising:
    forming an illumination area on a target to excite fluorescence from at least one point on the target;
    moving the illumination area on the target;
    forming a detection area on the target wherein the detection area is geometrically scaled to be larger than the illumination area;
    detecting the fluorescence emitted from the detection area on the target;
    moving the detection area in synchronization with the illumination area on the target; and
    shifting the detection area behind the illumination area of the target.

19. The method of claim 18, wherein the geometrical scaling provides a relationship between a size of the illumination area and a size of the detection area with respect to a direction of moving the illumination area and the detection area, wherein the size of both the illumination area and the detection area in a direction perpendicular to the moving direction is the same and the size of the detection area in the moving direction is defined by a gating time.

20. The method of claim 19, wherein the gating time is determined by a ratio of a width of the detection area and a velocity of the moving detection area.

21. The method of claim 18, further comprising a velocity of moving the illumination area that is determined by a ratio of a width of the illumination area and a fluorescence lifetime of the target.

22. The method of claim 18, wherein moving the detection area in synchronization with the illumination area on the target further comprises:
    moving the illumination area and the detection area in the same direction at an equal velocity.

23. The method of claim 18, wherein shifting the illumination area behind the detection area further comprises:
    shifting a leading edge of the detection area behind a trailing edge of the illumination area in the direction of the moving of both the illumination area and the detection area.

* * * * *